US010674921B2

United States Patent
Segman

(10) Patent No.: US 10,674,921 B2
(45) Date of Patent: Jun. 9, 2020

(54) METHOD AND DEVICE FOR COMPUTING OPTICAL HEMODYNAMIC BLOOD PRESSURE

(71) Applicant: CNOGA MEDICAL LTD., Caesarea (IL)

(72) Inventor: Yosef Segman, Caesarea (IL)

(73) Assignee: CNOGA MEDICAL LTD., Caesarea (IL)

( * ) Notice: Subject to any disclaimer, the term of this patent is extended or adjusted under 35 U.S.C. 154(b) by 577 days.

(21) Appl. No.: 15/325,108

(22) PCT Filed: Jan. 3, 2017

(86) PCT No.: PCT/IB2017/050008
§ 371 (c)(1),
(2) Date: Jan. 10, 2017

(87) PCT Pub. No.: WO2017/115343
PCT Pub. Date: Jul. 6, 2017

(65) Prior Publication Data
US 2018/0055381 A1 Mar. 1, 2018

Related U.S. Application Data

(60) Provisional application No. 62/273,489, filed on Dec. 31, 2015.

(51) Int. Cl.
*A61B 5/0205* (2006.01)
*A61B 5/0295* (2006.01)
(Continued)

(52) U.S. Cl.
CPC ............ *A61B 5/02028* (2013.01); *A61B 5/01* (2013.01); *A61B 5/0261* (2013.01);
(Continued)

(58) Field of Classification Search
CPC ... A61B 5/02028; A61B 5/01; A61B 5/02108; A61B 5/02125; A61B 5/02416;
(Continued)

(56) References Cited

U.S. PATENT DOCUMENTS 8,950,935 B1 2/2015 Khachturian et al.
9,717,417 B2 * 8/2017 DiMaio ................ A61B 5/0075
(Continued)

FOREIGN PATENT DOCUMENTS

DE 102012021940 5/2014

*Primary Examiner* — Navin Natnithithadha
(74) *Attorney, Agent, or Firm* — Mark M. Friedman

(57) ABSTRACT

Device for measuring blood pressure hemodynamically in blood vessels at one or more body locations comprising light source; at least three sensors including an array of at least three optical sensors, for receiving light and for obtaining a signal over time comprising temporal per pixel information for at least two wavelengths of light, and corresponding to a flow of blood within a blood vessel over time; a processing unit configured to receive the signal and generate a continuous dynamic blood pressure reading by using the temporal per pixel information for the at least two wavelengths of light to produce heart rate signals from the blood flow, and by applying a modified Windkessel model on the signal such that the blood pressure also depends on a spatial temporal pressure resistance function over time that depends on a body location of the blood flow over time, the pressure resistance function representing elastance/stiffness.

15 Claims, 13 Drawing Sheets

(51) Int. Cl.
*A61B 5/01* (2006.01)
*A61B 8/04* (2006.01)
*A61B 5/02* (2006.01)
*A61B 5/024* (2006.01)
*A61B 5/026* (2006.01)
*A61B 5/021* (2006.01)
*A61B 8/08* (2006.01)
*A61B 5/00* (2006.01)
*A61B 8/00* (2006.01)
*A61B 5/0215* (2006.01)
*A61B 5/053* (2006.01)

(52) U.S. Cl.
CPC ........ *A61B 5/0295* (2013.01); *A61B 5/02108* (2013.01); *A61B 5/02125* (2013.01); *A61B 5/02416* (2013.01); *A61B 5/02427* (2013.01); *A61B 5/6826* (2013.01); *A61B 8/04* (2013.01); *A61B 8/4416* (2013.01); *A61B 8/5223* (2013.01); *A61B 5/0205* (2013.01); *A61B 5/02154* (2013.01); *A61B 5/02438* (2013.01); *A61B 5/0535* (2013.01); *A61B 2562/063* (2013.01)

(58) Field of Classification Search
CPC . A61B 5/02427; A61B 5/0261; A61B 5/0295; A61B 5/6826; A61B 8/04; A61B 8/4416; A61B 8/5223; A61B 5/0205; A61B 5/02154; A61B 5/02438; A61B 5/0535; A61B 2562/063
USPC ........ 600/485, 486, 488, 483, 481, 500–504
See application file for complete search history.

(56) References Cited

U.S. PATENT DOCUMENTS

| | | | |
|---|---|---|---|
| 9,962,090 B2* | 5/2018 | DiMaio | A61B 5/0075 |
| 2006/0211930 A1* | 9/2006 | Scharf | A61B 5/14551 |
| | | | 600/336 |
| 2013/0324814 A1 | 12/2013 | Maarek | |
| 2014/0073931 A1 | 3/2014 | Galea et al. | |
| 2014/0213912 A1 | 7/2014 | Su | |
| 2015/0073230 A1 | 3/2015 | Stergiou | |
| 2015/0119725 A1 | 4/2015 | Martin et al. | |
| 2018/0296168 A1* | 10/2018 | Rice | A61B 5/7278 |

* cited by examiner

US 10,674,921 B2

METHOD AND DEVICE FOR COMPUTING OPTICAL HEMODYNAMIC BLOOD PRESSURE

FIELD AND BACKGROUND OF THE INVENTION

The present invention relates to apparatuses and methods for computing hemodynamic blood pressure, in some embodiments using optical sensors.

Hypertension is a major risk indicator for coronary heart diseases, renal failure, stroke and other various illnesses, and it is the primary global risk for mortality. Blood pressure measurements are essential to manage the risks resulting from hypertension or sudden stroke.

Hypertension is a worldwide disease that is spreading. Its prevalence has been rising over the years. Today it is the primary global risk factor for mortality, and causes about 13% of deaths worldwide. High blood pressure levels are related to peripheral artery diseases, renal deficiency, retinal hemorrhage and visual impairment. Observational epidemiological studies have shown interdependence between blood pressure and vascular mortality, consequently the "prehypertension" range is also being investigated during the recent years. This "prehypertension" range, i.e. 120 to 139 mm Hg for the systolic blood pressure and 80 to 89 mm Hg for the diastolic blood pressure, was found to be quite frequent in the world population and may also lead to coronary heart disease and cardiovascular disease. As a result, blood pressure measurements may act as a risk indicator for various diseases and monitoring it may postpone or even prevent those illnesses. Today, the common technique for measurement is the oscillometric technique, due to its convenience and availability. Frequent home blood pressure measurements can foresee morbid events better than the occasional clinical monitoring, and can also overlook the 'white coat effect', a known phenomenon of an increase in the blood pressure in the presence of a physician.

SUMMARY OF THE PRESENT INVENTION

One aspect of the present invention is a device for measuring blood pressure hemodynamically in blood vessels at one or more body locations of a mammalian subject, the mammalian subject having a tissue, comprising a light source for shining light at the tissue under consideration; at least three sensors including an array of at least three optical sensors, for receiving light that traversed and/or was reflected from the tissue and for obtaining a signal over time, wherein the signal obtained by the array of sensors comprises temporal per pixel information for at least two wavelengths of light, the signal corresponding to a flow of blood within a blood vessel of the subject over time; hardware and software for supporting the at least three sensors and for converting the signal to a digital form in the event at least one of the at least three sensors is analog, the hardware and software also comprising a processing unit configured to receive the signal and generate a continuous dynamic blood pressure reading by using the temporal per pixel information for the at least two wavelengths of light to produce heart rate signals from the blood flow, and by applying a modified Windkessel model on the signal such that the blood pressure also depends on a spatial temporal pressure resistance function over time, wherein the pressure resistance function over time depends on a body location of the blood flow over time, and wherein the pressure resistance function represents (i) elastance, (ii) stiffness or (iii) elastance and stiffness, of the blood vessel at a given body location and at a given time.

In some embodiments the light source is configured to shine light whose wavelength has any of the following ranges: visual range of 0.3 micron to 0.7 micron, near IR range of 0.7 micron to 5 micron, mid IR range of 5 micron to 40 micron and far IR range of 40 micron to 350 micron.

In some embodiments the processing unit is configured to produce the heart rate signals by averaging the per pixel information of the array per given time.

In some embodiments the processing unit is configured to determine the hemodynamic blood pressure measurement using a resistance equation (21) of the form $$G(t) = \pm \frac{\alpha}{R_0}(t - t_d)^n,$$

where $t_d > 0$, $\alpha$ and $R_0$ are constants and n=0, 1, 2, 3, 4 ..., .

In some embodiments, while the signal over time is obtained, the array of at least three optical sensors and/or one or more additional sensors are configured to also obtain and the processing unit is configured to also receive and process for increased accuracy of a blood pressure reading, at least one of the following: (a) local tissue perfusion using an optical sensor, (b) local tissue temperature using an optical sensor or thermometer, (c) volume and density of the blood tissue in the body location $X_0$ at which at least one optical sensor or ultrasound sensor is used.

In some embodiments, while the signal over time is obtained, the array of at least three optical sensors and/or one or more additional sensors are configured to also obtain and the processing unit is configured to also receive and process for increased accuracy of a blood pressure reading, at least two of the following: (a) local tissue perfusion using an optical sensor, (b) local tissue temperature using an optical sensor or thermometer, (c) volume and density of the blood tissue in the body location $X_0$ at which at least one optical sensor or ultrasound sensor is used. In some embodiments, while the signal over time is obtained, the array of at least three optical sensors and/or one or more additional sensors are configured to also obtain and the processing unit is configured to also receive and process for increased accuracy of a blood pressure reading all of the following: (a) local tissue perfusion using an optical sensor, (b) local tissue temperature using an optical sensor or thermometer, and (c) volume and density of the blood tissue in the body location $X_0$ at which at least one optical sensor or ultrasound sensor is used.

In some embodiments, the processing unit is configured to provide the blood pressure at a particular body location, $X_0$, of the mammalian subject, wherein the pressure resistance function is a spatial temporal function that measures the resistance or elastance of the blood vessel at the particular body location, $X_0$, over time.

In some embodiments, the device further comprises an ultrasound component configured to emit and receive ultrasound waves at the tissue of the blood vessel at the local location $X_0$ and to generate one or more signals corresponding to (a) the volume and/or density of the tissue at the particular body location and (b) a volume velocity of the blood flow in the tissue, wherein the processing unit is configured to receive output from the ultrasound component to increase an accuracy of a blood pressure reading by estimating an initial blood pressure reading.

In some embodiments the processing unit is configured to use the temporal per pixel information for the at least two wavelengths of light to produce at least one of (i) temporal histograms of light intensity for each wavelength of the at least two wavelengths and (ii) averaging the per pixel information of the array per given time.

In some embodiments the processing unit is configured to use the temporal per pixel information for the at least two wavelengths of light to produce temporal histograms of light intensity for each wavelength of the at least two wavelengths.

In some embodiments the processing unit is configured to apply algebraic operations to the temporal per pixel information for the at least two wavelengths of light.

Another aspect of the present invention is a method for measuring blood pressure hemodynamically in blood vessels at one or more body locations of a mammalian subject, the mammalian subject having a tissue, comprising using a light source, shining light at the tissue under consideration; providing at least three sensors including an array of at least three optical sensors, for receiving light that traversed and/or was reflected from the tissue and for obtaining a signal over time, wherein the signal obtained by the array of sensors comprises temporal per pixel information for at least two wavelengths of light, the signal corresponding to a flow of blood within a blood vessel of the subject over time; providing hardware and software for supporting the at least three sensors and for converting the signal to a digital form in the event at least one of the at least three sensors is analog; and providing a processing unit configured to receive the signal and generate a continuous dynamic blood pressure reading by using the temporal per pixel information for the at least two wavelengths of light to produce heart rate signals from the blood flow, and by applying a modified Windkessel model on the signal such that the blood pressure also depends on a spatial temporal pressure resistance function over time, wherein the pressure resistance function over time depends on a body location of the blood flow over time, and wherein the pressure resistance function represents (i) elastance, (ii) stiffness or (iii) elastance and stiffness, of the blood vessel at a given body location and at a given time.

These and other features, aspects and advantages of the present invention will become better understood with reference to the following drawings, descriptions and claims.

BRIEF DESCRIPTION OF THE DRAWINGS

Various embodiments are herein described, by way of example only, with reference to the accompanying drawings, wherein.

DETAILED DESCRIPTION OF THE INVENTION

The following detailed description is of the best currently contemplated modes of carrying out the invention. The description is not to be taken in a limiting sense, but is made merely for the purpose of illustrating the general principles of the invention, since the scope of the invention is best defined by the appended claims.

The present invention generally provides a device and method for monitoring blood pressure based on real time color photography of the blood tint diffusion. This provides a new hemodynamic optical method and device/system for measuring blood pressure noninvasively, using the temporal color distribution image of the skin tissue. Applicant's first prototype was a camera that photographed the face color distribution by using color video stream. The reflected light from the patient tissue provided rich information about the human physiological and emotional condition. In accordance with one embodiment of the present invention, the device is configured to measure the internal arterial blood pressure from the capillary hemodynamics. The device is sealed to external light in one embodiment. The device radiates light at different wavelengths traversing (in one embodiment) the finger capillary tissue and then projecting the light onto the color image sensor. The image is then analyzed by dedicated DSP algorithms for computing various bio parameters and then displayed on the screen.

The present invention is a non-invasive hemodynamic method, system and device for computing blood pressure, by using color imaging resulting from a set of light, for example monochrome light, that transverses through the tissue under consideration. Applicant has found that the variation in the pressure flow can be determined from the changes in the height of the temporal color histograms and additional temporal volume information. The analytical solution of the Windkessel model provides additional insight on the resistance function. This new technique was clinically evaluated as part of Applicant's new device, the TensorTip. Clinical evaluation and the new method and device successfully fulfilled the ISO 81060-2 recognized standard requirements. The device, method and system of the TensorTip performed quite well in clinical trials both for standard blood pressure measurements and also for individuals that were subject to alterations of blood pressure following cardiac surgery.

Figure 1A:
FIG. 1A is a photo showing a perspective view of a device that measures blood pressure among other bioparameters accompanied by, in accordance with one embodiment of the present invention.

In contrast to prior art methods of measuring blood pressure, the device and method of the present invention measures the blood pressure both noninvasively and without having to pump air, which is less convenient. The extra convenience of measuring blood pressure by merely inserting one's finger into a relatively small, in some embodiments portable, device has the advantage over some prior art methods in that it allows the subject to do other things at the same time. In further contrast to the prior art, the device, system and method of the present invention measures the blood pressure continuously and dynamically in certain embodiments. In some embodiments, the device is also small, light-weight and portable. Furthermore, in preferred embodiments, the device is intended for use in the home environment and as well as in medical clinics either as an additional method of measuring blood pressure or as the primary method of measuring blood pressure. The TensorTip device, as shown in FIG. 1A, comprises a Digital Signal Processor (DSP) medical and control subsystems as presented in FIG. 1B. In certain embodiments, the medical subsystem contains a color image sensor, light sources, for example LEDs, and a Digital Signal Processor (DSP) which is responsible for the image acquisition, the image processing, the lighting self-test and the extraction of the clinical parameters' values. The control subsystem, in one particular embodiment, contains four touch-buttons, a display, an audio-speaker and a Microcontroller Unit (MCU) which is in charge of the user interface, the process management, the internal storage and the device's power management. The device also includes, in certain embodiments, a thermometer for measuring the local temperature of the tissue, for example tissue from a finger or an earlobe, examples of a body part used for tissue, that the light reflects from. The device of the present invention further includes, in certain embodiments, an ultrasound device configured to emit and/or receive ultrasound waves at the tissue and to generate one or more signals corresponding to (a) the volume and/or density of the fingertip or other body part where the tissue is and (b) the flow. The flow, in one embodiment, is the volume velocity of the blood flow in the tissue that the light reflects/traverses. In still further contrast to most of the prior art models known today, which use a single resistance functional Windkessel model, the present device, method and system utilizes an extended model, considers more complex considerations. Specifically, in some embodiments of the present invention, the processing unit is configured to receive at least one signal from at least one sensor and generate a continuous dynamic blood pressure reading by applying a modified Windkessel model on the at least one signal such that the blood pressure also depends inversely on a pressure resistance function over time rather than on a constant resistance, wherein the pressure resistance function over time depends on a body location of the fluid over time, and wherein the pressure resistance function is a measure of an elastance of the blood vessel at a given body location and at a given time. The present invention in some embodiments uses a color array sensor which enables providing richer information using light traversing the object. In contrast to prior art devices and methods for measuring blood pressure, the device and method of the present invention is simple to use and does not need any air pumping. In contrast to the prior art devices, the device of the present invention in some embodiments uses a color array sensor which allows richer information to be provided compared to a standard pulse oximetry since a standard pulse oximeter usually uses two discreet diode sensors and light source(s), for example two monochromatic light sources. The device of the present invention in some embodiments measures blood pressure dynamically, continuously and conveniently in a practical manner for patients at home and/or without the need for assistance by doctors, nurses, technicians or other medical caregivers.

The principles and operation of a Method and Device for Computing Optical Hemodynamic Blood Pressure may be better understood with reference to the drawings and the accompanying description.

Figure 1B:
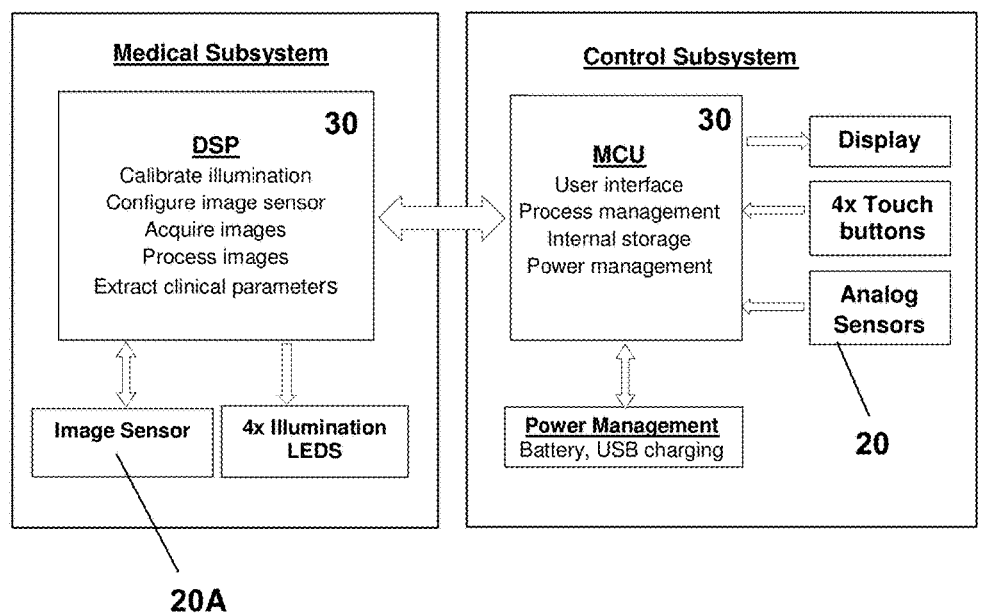
FIG. 1B is a high-level schematic block diagram that shows a medical subsystem used in the device of FIG. 1A on the left and a control subsystem used in the device of FIG. 1A on the right, in accordance with one embodiment of the present invention.

FIG. 1A shows the TensorTip device 10, in accordance with one embodiment. FIG. 1B is a functional illustration that depicts the software roles and interfaces of the device, in accordance with one embodiment of the present invention. The device 10 measures blood pressure using hemodynamics, which is different from how other instruments in this field measure blood pressure. Hemodynamics is used in numerous medical fields, mostly during a surgical procedure or afterwards, wherein the blood pressure is measured by an in-line arterial tube.

Figure 2:
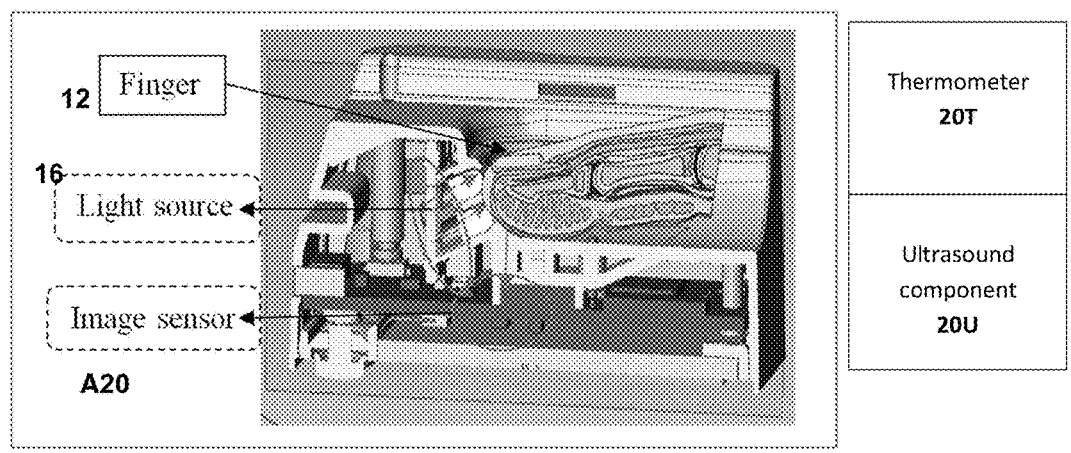
FIG. 2 is a sectional view showing the inside of a device as in FIG. 1A from the side, in accordance with one embodiment of the present invention.

As seen from the cross-sectional view of FIG. 2, the device 10 comprises, in one embodiment, a finger compartment 12 for receipt of a subject's finger (in other embodiments the compartment is configured to receive an earlobe of the subject), at least one light source 16, which in some embodiments is at least one monochromatic light sources (for example one or in other embodiments two, or three, or four monochromatic light sources) in the visual to IR spectrum (~600 nm to ~1000 nm), for example four such light sources, and an optical sensor such as a color image sensor 20A. The device 10 produces a lossless stream of video signal, for example color video signal, and uses the image buffer memory and the dedicated DSP processor for internal computations. In one embodiment, the device 10 incorporates the system, methods and/or devices, including algorithms, used for the biomarkers computation as described in U.S. Pat. Nos. 8,335,550 and 8,792,948 issued to Applicant. As seen from FIG. 2, device 10 may also comprise a thermometer 20C and an ultrasound sensor 20B.

Figure 3A:
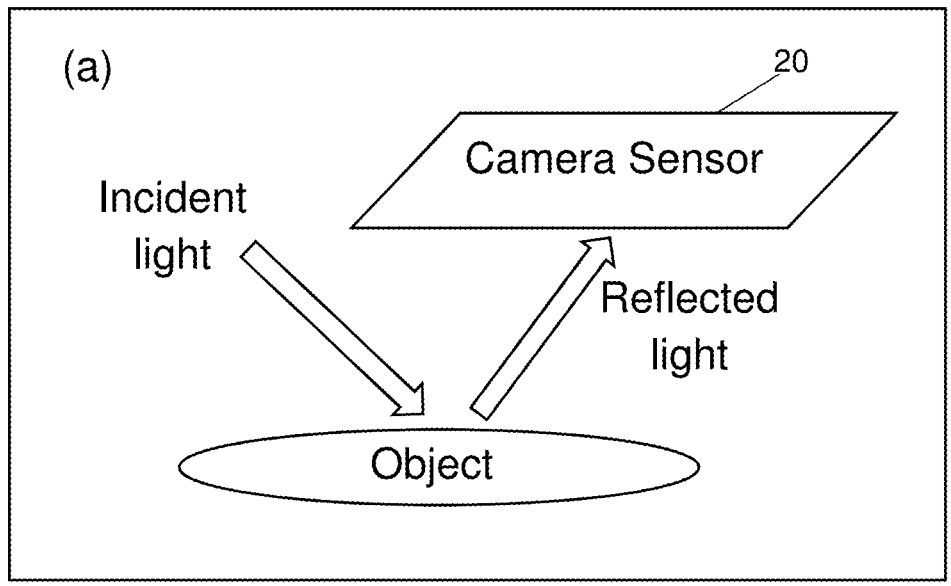
FIG. 3A is schematic of the flow of light using a method, system or device that utilizes light reflected off an object, in accordance with one embodiment of the present invention.
Figure 3B:
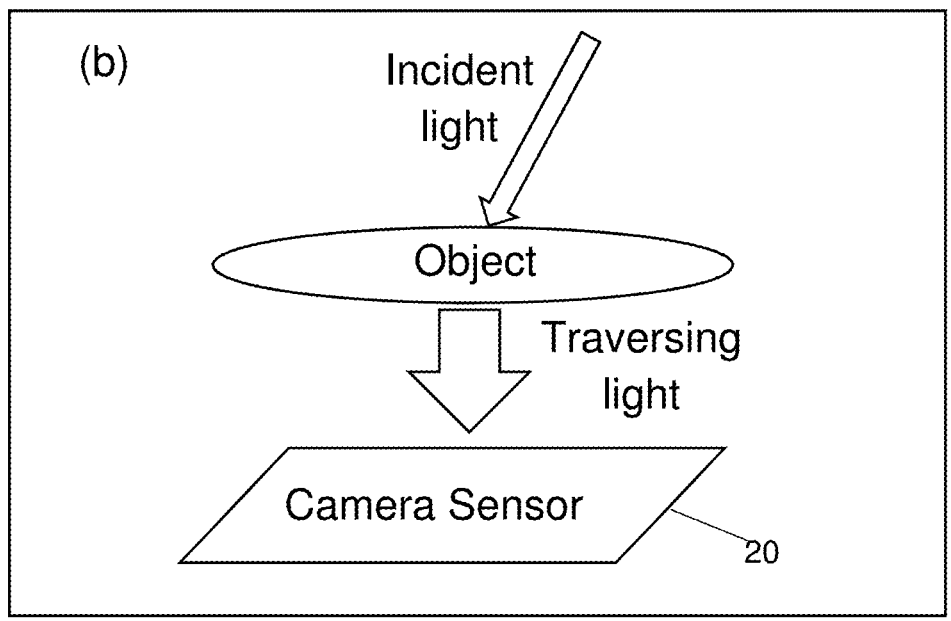
FIG. 3B is schematic of the flow of light using a method, system or device that utilizes light traversing an object, in accordance with one embodiment of the present invention.

The relationship between the light source 16 and the array of optical sensors 20A, which may include a color image sensor 20A, can be implemented in one of two ways, as shown in FIG. 3A and FIG. 3B. FIG. 3A shows incident light is being reflected from an object such as a finger and FIG. 3B shows incident light traversing the object. The first way, as shown in FIG. 3A, which was Applicant's first prototype, is based on ambient light being reflected from a tissue onto the sensor(s) 20, for example image sensor 20A, and the tissue can be the skin tissue of the subject or for example internal tissue of the subject during endoscopic photography. In contrast, in FIG. 3B, a real time optical sensor 20A, which may be a color image sensor 20A, provides the ability to analyze tissue pigmentation over spatial-temporal-color domain using the light that traverses the tissue, such as tissue of a fingertip or earlobe. The optical sensor 20A of the present invention in one embodiment uses a color array sensor which allows richer information to be provided compared to a standard pulse oximetry since a standard pulse oximeter usually uses two discrete diode sensors and light source(s), for example two monochromatic light sources.

Image Sensor 20:

Applicant's method and device of the present invention is based on at least three sensors 20, which includes an array of at least three optical sensors 20, for example a color image sensor 20A. In one embodiment, the optical sensor 20 is an image sensor 20A and is sensitive to a continuous spectrum of light in the range of ~380 nm-~1000 nm. In other embodiments one or more of the sensors are optical sensors that are not image sensors, and in that case the optical sensors, in one embodiment, are sensitive to light in any of the following ranges: visual range of 0.3 micron to 0.7 micron, near IR range of 0.7 micron to 5 micron, mid IR range of 5 micron to 40 micron and far IR range of 40 micron to 350 micron. The sensor 20 may be utilized for applications, such as medical monitoring, cosmetic diagnosis, lifestyle, automobile, security, etc. The embodiment described herein involves the applications of medical monitoring with focus on blood pressure.

Figure 4:
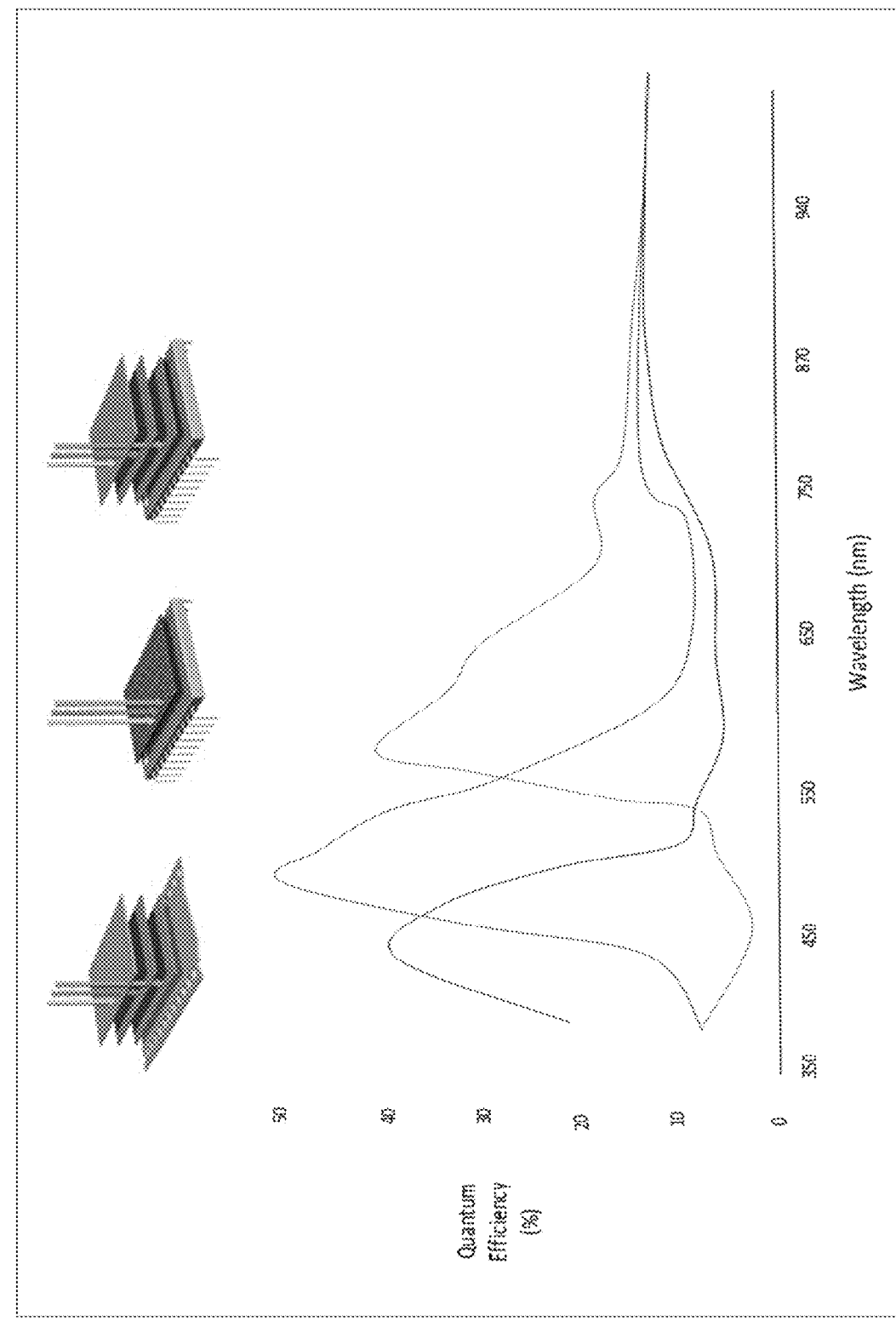
FIG. 4 is a graph of color image sensor spectra efficacy, showing quantum efficiency for each of three wavelengths (R, G, B) of light, in accordance with one embodiment of the present invention.

FIG. 4 shows the image sensor spectra efficiency used in the device 10 of the present invention and showing three colors, blue, green and red. Since the drawings are in black and white, to locate the "colors" on the graph of FIG. 4, it is noted that the spectra corresponding to the blue color starts around the low 20s, the spectra corresponding to green light has the highest maximum quantum efficiency and the two spectra corresponding to red and green both start at a little less than 10.

Color Stream Video:

Real time stream video provides spatial-temporal-color information consists of a six dimensional space: three dimensions of color (Red, Green and Blue); two dimensions of position (x and y) and one dimension of time (t). In order to detect small changes in the blood flow and in color pigmentation, a high accuracy dynamic range (i.e. number of bits per pixel), wavelength range and frames per second (FPS) are needed.

Mathematical Model a) Preliminary

The color image sensor provides triple spatial-temporal functions in the form of $$R(x,y,t), G(x,y,t) \text{ and } B(x,y,t) \qquad 1.$$

for each set of Light Source (L) we denote by $$R_L(x,y,t), G_L(x,y,t) \text{ and } B_L(x,y,t) \qquad 2.$$

The value of each color represents the dynamic range of the image sensor; in our case, 12 bits per color, giving a total of 36 bits. The spatial information i.e. pixel position is represented by x and y and t represents the time dimension. The image sensor is used as a 3D-Spectrometer and Color Distributor.

Based on our investigation of the skin or blood tissues Applicant has found that under Normal Light Condition, i.e. day light, they will have the color intensity order of Red>Green≥Blue and in some cases Red>Blue≥Green. This phenomenon is demonstrated in FIG. 5. The figure shows the histograms of actual blood tissue pigments observed at the red to IR wavelengths emitted from 4 LED lights. As can be seen there, the red histogram is the dominated one, followed by the green and then by the blue. This phenomenon is attributed to the iron in the hemoglobin that causes the blood to be red. The tissue tint depends on oxygen, carbon dioxide and other blood components. Nonetheless, the horseshoe crab has blue blood due to hemocyanin in his blood. Instead of iron hemocyanin contains copper that bonds to the oxygen. Therefore, the copper is responsible for the blue blood.

b) Color Coordinate System

In some cases it is useful to use different color coordinate system. Here are two examples (we use i,j,t for discrete location instead of x,y,t):

$$R_{new}(i, j, t) = \frac{R(i, j, t)}{S(i, j, t)}$$

$$G_{new}(i, j, t) = \frac{G(i, j, t)}{S(i, j, t)}$$

$$B_{new}(i, j, t) = \frac{B(i, j, t)}{S(i, j, t)}$$

Where $$S(i,j,t) = R(i,j,t) + G(i,j,t) + B(i,j,t) \qquad 4.$$

as for the first example, and a normalization over the 2-D sphere embedded in 3-D dimension (regarded as $S^2$) is considered as the second example, i.e.

$$S(i,j,t) = \sqrt{R^2(i,j,t) + G^2(i,j,t) + B^2(i,j,t)} \qquad 5.$$

Having color coordinate transformation over a unit sphere, normalizing the magnitude of all pixels.

c) Temporarily Color Histogram (TCH)

The TCH is an important tool for describing changes in the space-time-color domain.

Let $$R_L(x,y,t), G_L(x,y,t) \text{ and } B_L(x,y,t) \qquad 6.$$

be three color domains representing Red, Green and Blue spatial-temporal-color functions associated with a set of light emissions L. We define triple continuous weighted histograms for each color as the Lebesgue-Dirac integral function.

$$H_r(p, t) = \int_{R^2} \delta(R(x, y, t) - p) dE_r(x, y),$$

$$H_g(p, t) = \int_{R^2} \delta(G(x, y, t) - p) dE_g(x, y),$$

$$H_b(p, t) = \int_{R^2} \delta(B(x, y, t) - p) dE_b(x, y)$$

where H represents the temporary histogram volume of the red, green and blue images (color plane) respectively. E represents a measurable weighted function and p is the pixel value. The delta function becomes zero whenever a color pixel value does not match the p pixel value.

A discrete form of Eq. 7 is $$H_r(R(i, j, t)) = H_r(R(i, j, t)) + \left\{ \begin{array}{c} \text{if } R(i, j, t) \geq 0, 1 \\ \text{else, } 0 \end{array} \right\},$$

for all red pixels $$H_g(G(i, j, t)) = H_g(G(i, j, t)) + \left\{ \begin{array}{c} \text{if } G(i, j, t) \geq 0, 1 \\ \text{else, } 0 \end{array} \right\},$$

for all green pixels $$H_b(B(i, j, t)) = H_b(B(i, j, t)) + \left\{ \begin{array}{c} \text{if } B(i, j, t) \geq 0, 1 \\ \text{else, } 0 \end{array} \right\},$$

for all blue pixels

In terms of the discrete signal while dE=1, $H_r(p,t)$ represents the number of red pixels having p value at time t. Respectively, $H_g(p,t)$ and $H_b(p,t)$ representing the green and blue temporary histograms. FIG. 5 shows three temporary color histograms.

Figure 5A:
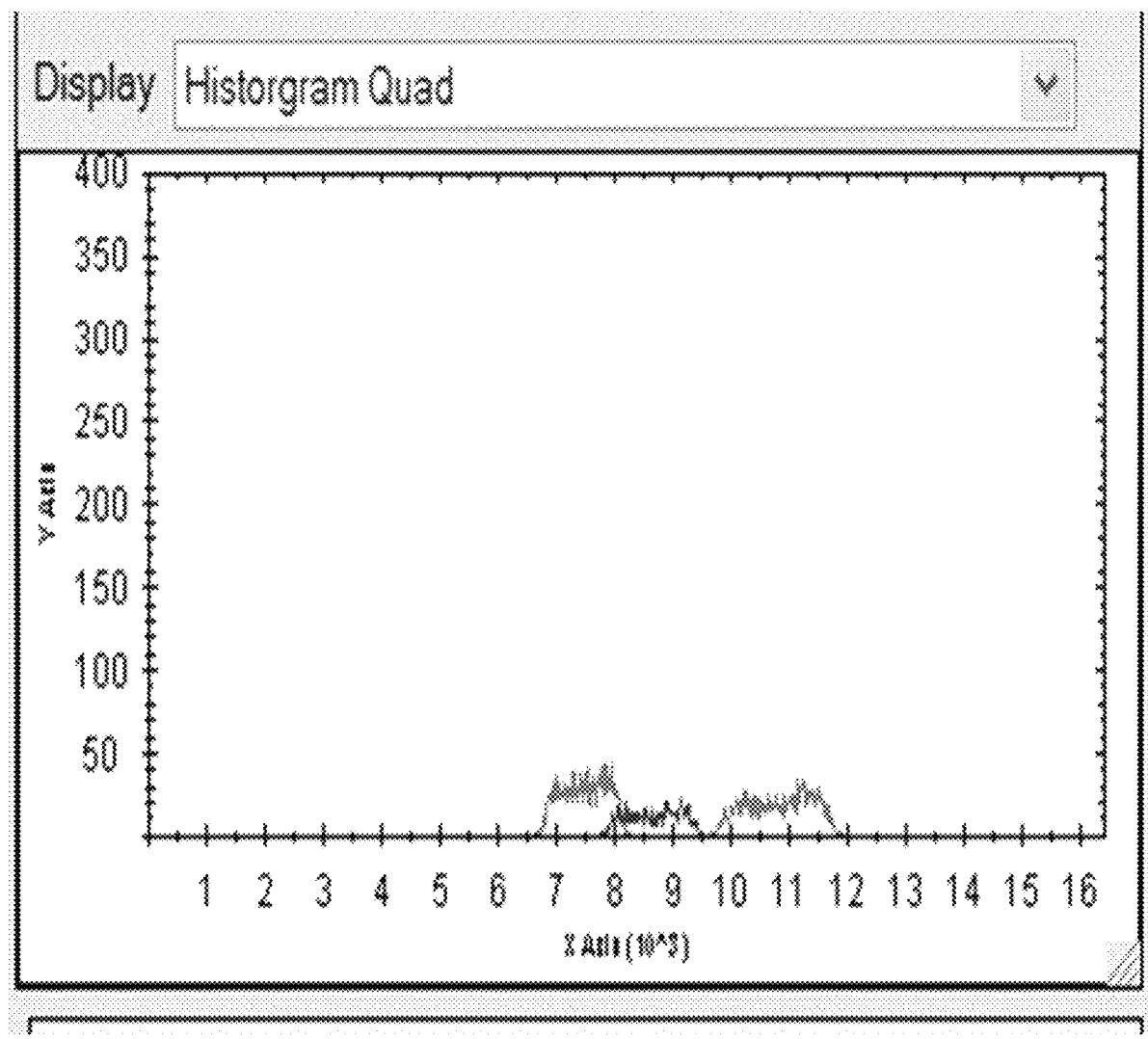
FIG. 5A is a histogram of the three wavelengths of FIG. 4, in accordance with one embodiment of the present invention.

FIG. 5A: Three temporary color histogram plots which clearly show that the distribution absorption level along the horizontal axis satisfies the order of q(Red)≥q(Green)≥q(Blue), where q denotes a distribution function. Since these drawings are black and white, for clarity it is noted that in FIG. 5A and in FIG. 5B, going from left to right in each drawing, the respective histogram plots are blue, then green and then red. For example, in FIG. 5A, the blue plot spans from about 6.5 to about 8 and ⅙ along the X axis, the green is from about 7 and ¾ to about 9 and ½ along the X axis and the red is from about 9 and ½ to about 12 along the X axis.

Figure 5B:
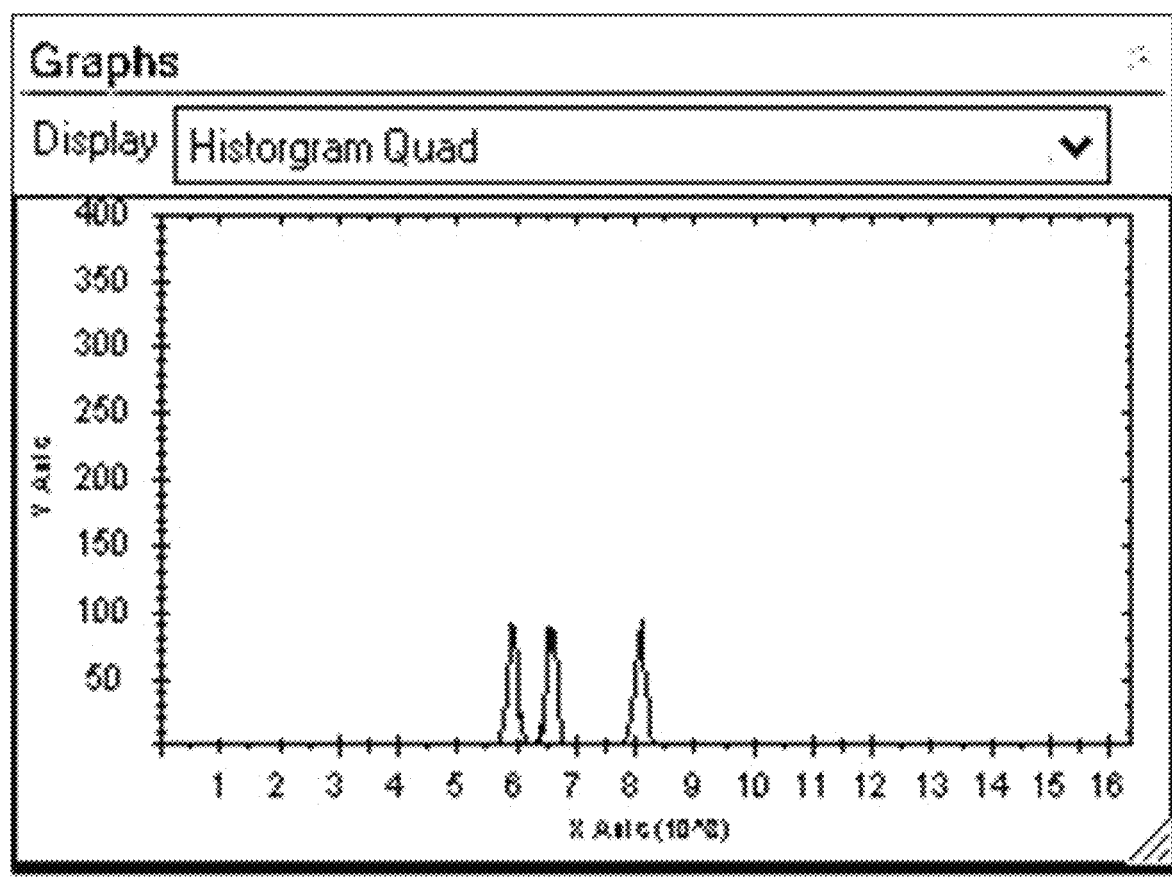
FIG. 5B is a histogram of the three wavelengths of FIG. 4 but showing a narrow dynamic range compared with FIG. 5A, in accordance with one embodiment of the present invention.

FIG. 5B: A Narrow Dynamic Range Compared with FIG. 5A.

The color histograms have a few elements that are configured to represent biological parameters; in certain embodiments (i) Height change represents the variation in volume of the optical pressure flow projected onto the image sensor; (ii) The horizontal axis represents the pixel value, the shift of the histogram sideways represents the pulse; (iii) The location of the histogram over the horizontal axis signifies the 3D absorption level; (iv) The spatial-temporal-color absorption may indicate on certain hemodynamics, blood count and chemistry and (v) A possibility to detect the peripheral heart pulse by the movement of the histograms along the p axis (horizontal axis).

d) Peripheral Pulse Temporal Waveform $$Pw_r(t) = \frac{1}{MN} \sum_{(i=1, j=1)}^{(M,N)} R(i, j, t)$$

$$Pw_g(t) = \frac{1}{MN} \sum_{(i=1, j=1)}^{(M,N)} G(i, j, t)$$

$$Pw_b(t) = \frac{1}{MN} \sum_{(i=1, j=1)}^{(M,N)} B(i, j, t)$$

Where $Pw_{rgb}(t)$ represents the average of the spatial color plane under consideration, M stands for the total rows and N for total columns. M×N is the pixel resolution of the image. Three heart rate pulse signals may be used by averaging each spatial color plane.

e) Basic Principle of the Blood Pressure Calculation:

The two element Windkessel model is given by the following ordinary differential equation (ODE)

$$F(t) = \frac{P(t)}{R} + c \cdot \frac{dP}{dt}$$

Eq. 10 has direct solution of the form (see annex A)

$$P(t) = c^{-1} \cdot e^{-\frac{\alpha(t-\tau_d)}{c \cdot R}} \cdot \int e^{\frac{\alpha(t-t_d)}{c \cdot R}} \cdot F(t) \cdot dt + c_1 \cdot e^{-\frac{\alpha(t-t_d)}{c \cdot R}};$$

$$c_1 = \frac{L}{C}, L \text{ is } const.$$

Note that the free integral is a function of t. When flow F(t)=0, the added exponential function represents the aorta diastole pressure i.e.

$$P_d(t) = \frac{L}{C} \cdot e^{-\frac{\alpha(t-t_d)}{c \cdot R}}$$

There are few feasible scenarios on the diastolic pressure i.e. Eq. 12. The average diastolic pressure is a positive constant achieved at $t=t_d$, where $t_d$ represents the collapsing of F(t) to idle systolic flow, which may be considered F(t)=0 for a normalized F. In other words, the local minimum value of F is normalized to zero. Thus, in this case $P_d(t)$ is a positive constant representing the diastolic pressure at rest (i.e. idle flow) which leads to $$P_d(t) = \frac{P(t_d)}{C} \text{ where } L = P(t_d) \text{ and } t = t_d$$

For $t > t_d$, the part depending on the diastolic contributes $$P_d(t) = \frac{P(t_d)}{C} \cdot e^{\frac{-\alpha(t-t_d)}{c \cdot R}}$$

while the initial pressure $P(t_d)$ represents the aortic diastolic pressure at $t_d$.

The Windkessel model assumes constant resistance R (Eq. 10). This assumption may not be suitable in case of mammalian blood pressure, where resistance may change over various body location and time. The resistance strongly depends on the local vessel elasticity or stiffness, even though in the most severe scenarios of blood vessels stiffness, certain local flexibility still exists and therefore may generate functional resistance.

A spatial-temporal resistance function of Eq. 10 leads to the following form, $$F(X,t) = \frac{P(X,t)}{R(X,t)} + c \cdot \frac{\partial P(X,t)}{\partial x_j} \frac{dP(X,t)}{dt} = P(X,t) \cdot G(X,t) + c \cdot \frac{\partial P(X,t)}{\partial x_j} \frac{dP(X,t)}{dt}$$

Where $X=(x_1,x_2,x_3)=(x,y,z)$ and where c is a constant and where $R(X,t)$ is the resistance caused by the stiffness of the vessel, i.e. the vessel walls, and $$G(X,t) = \frac{1}{R(X,t)}$$

and X represents a body location (this is the spatial component). The above model takes under consideration a change in the location as well as a change in time. For the purpose of the present invention considering a temporal function at fixed location $X=X_0$ $$F(t) = \frac{P(t)}{R(t)} + c \cdot \frac{dP}{dt} = P(t) \cdot G(t) + c \cdot \frac{dP}{dt}$$

Where, $G(t)$ reflects 1-D temporal resistance function (Eq. 16), i.e.

$$G(t) = \frac{1}{R(t)}$$

Eq. 16 is a linear order differential equation which has a direct solution in the form of:

$$p(t) = c^{-1} \cdot e^{-c-1\int G(t)dt} \cdot \int e^{c-1\int G(u)du} \cdot F(t) \cdot dt + c_1 \cdot e^{-c-1\int G(t)dt}$$

where $$C_1 = \frac{L}{C}$$

(For detailed solution see annex A)

The Laplace domain of Eq. 16 takes the following form $$\hat{F}(s) = [\hat{P} * \hat{G}](s) + c \cdot s \cdot \hat{P}(s) - P(0) \qquad 20.$$

Where the sign '*' means a convolution over the Laplace domain. The main reason for using Laplace transform is attributable to the initial conditions at $P(0)$. Although using the Laplace domain may provide an additional way for extracting blood pressure, it will not be discussed here.

Functional resistance (i.e. Eq. 16) may provide wider consideration to Eq. 10. Considering various polynomial orders of $G(t)$ by associating $$G(t) = \pm \frac{\alpha}{R_0}(t-t_d)^n,$$

where $t_d>0$ is a constant and $n=0, 1, 2, 3, 4 \ldots$.

The case of $n=0$ is considered in Eq. 9 and the solution thereof is given in Eq. 10. The case of $n=1$ provides a Gaussian shape resistance function. $R_0$ is considered the temporal initial resistance or base resistance constant. This solution leads to the following model $$P(t) = c_1 e^{-\frac{\alpha}{2R_0}(t-t_d)^2 - k} \int e^{\frac{\alpha}{2R_0}(t-t_d)^2 + k} F(t)dt + c_2 e^{-\frac{\alpha}{2R_0}(t-t_d)^2 - k}$$

$$= c_1 e^{-\frac{\alpha}{2R_0}(t-t_d)^2} \int e^{\frac{\alpha}{2R_0}(t-t_d)^2} F(t)dt + c_2 e^{-\frac{\alpha}{2R_0}(t-t_d)^2 - k}$$

$$= c_1 e^{-\frac{\alpha}{2R_0}(t-t_d)^2} \int e^{\frac{\alpha}{2R_0}(t-t_d)^2} F(t)dt + c_2 e^{-\frac{\alpha}{2R_0}(t-t_d)^2}$$

The free coefficient depending on k is integrated within the coefficient $C_2$ i.e. $c_2 = c_1 e^{-k}$.

23. Eq. 21 can be estimated as follows $$P(t) = c_1 e^{-\frac{\alpha}{2R_0}(t-t_d)^2} \int e^{\frac{\alpha}{2R_0}(t-t_d)^2} F(t)dt + c_2 e^{-\frac{\alpha}{2R_0}(t-t_d)^2}$$

$$\cong c_1 e^{-\frac{\alpha}{2R_0}(t-t_d)^2} \cdot E \cdot FD + c_2 e^{-\frac{\alpha}{2R_0}(t-t_d)^2}$$

$$= e^{-\frac{\alpha}{2R_0}(t-t_d)^2} (c_1 E \cdot FD + c_2)$$

Where the constant $$E = e^{\frac{\alpha}{2R_0}T^2}, T = \text{Max}(t_e - t_d, t_d - t_s) \text{ and } FD = \sum_{t=T_s}^{T_e} \Delta F_t$$

is a simple rectangle integral approximation.

Figure 6:
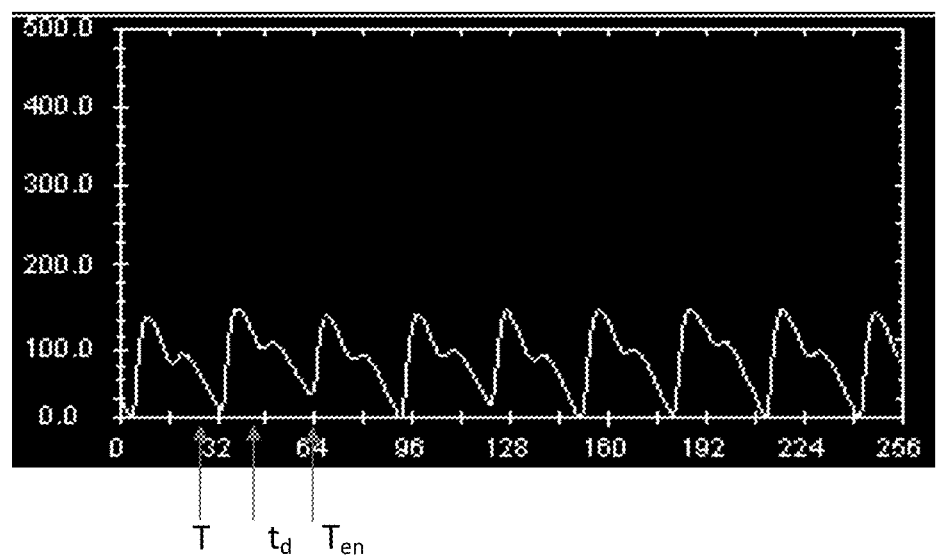
FIG. 6 shows a device's display screen of a subject's blood pressure on a device, wherein $T_s$ is a normalized starting point of the systolic blood pressure, $T_d$ represents the max local systolic, and $T_e$ the final normalized end point of the systolic, in accordance with one embodiment of the present invention.

FD represents an approximation of the beat2beat volume change of $F(t)$ in the time interval $T=(t_e-t_s)$. Eq. 22 may provide a rough estimation of the beat2beat blood pressure flow. FIG. 6 depicts this idea.

FIG. 6: In accordance with one embodiment of the present invention, $T_s$ represents the normalized starting point of the systolic blood pressure, $T_d$ represents the max local systolic, and $T_e$ the final normalized end point of the systolic.

Eq. 18 is a theoretical and practical consideration for a Gaussian shape resistance function. Other potential polynomial degree or other resistance functions can be used. In addition, the above rough integral approximation could easily be improved. In practice, in order to compute the blood pressure (Systolic and Diastolic), additional information is required and a certain state machine is needed to take care of the emitted light, the absorption level, a-priori data information, etc.

Other machines may use the combination of Oscillometric blood pressure and hemodynamic flow, whereas the Oscillometric blood pressure may provide initial blood pressure and certain indications for the continuous hemodynamic blood pressure estimation.

Equation 15 is an extension of the Windkessel model that takes into consideration the stiffness of the vessel. Equations 19, 21 and 22 are important solutions f) Initial Blood Pressure The first hemodynamic blood pressure measurement is an important measurement and requires special considerations. One (or more) of the following bioparameters is used in the calculation of the initial blood pressure and in particular in the determination of the coefficients $\alpha$ and $R_0$: (a) local tissue perfusion, (b) local tissue temperature, (c) peripheral pulse waveform flow, (d) absorption levels, (e) light energy emitted at various wavelength, (f) device temperature, (g) pulse, etc.

A state machine considering the above points, various situations of the temporal blood pigmentation and pre-study have been used by Applicant to determine various resistance parameters in order to compute the best possible initial blood pressure reading. In one particular non-limiting embodiment, the one (or more) of the above bioparameters used in determination of the coefficients $\alpha$ and $R_0$ are obtained from a continuous analog signal of such bioparameter(s), for example from the ultrasound device, from the thermometer or from a known device such as an oximeter on the finger. Alternatively, in one other non-limiting embodiment, an ECG may also be used as the other device to provide the continuous analog signal but in that case certain manipulation of the data is first necessary, such as taking the integral of the ECG wave output.

In certain embodiments, the volume and/or density of the tissue of the body part, for example the thickness of the fingertip providing the volume of the tissue, is obtained from an output of the ultrasound device or from the histogram itself. For example, the blood flow, for example volume velocity, of the blood at the fingertip or other body part, is obtained from the ultrasound device. The analog temperature is obtained from a thermometer, although a digital temperature reading can be obtained from other sources such as an optical sensor.

This information is useful for the present invention because the greater the temperature of the tissue of the body part of the subject, the more blood cells in that tissue, and hence the better the signal accuracy of the first (and later) hemodynamic blood pressure measurement. Likewise, knowing the volume and/or density of the tissue (obtained from the ultrasound sensor or optical sensor) provides better signal accuracy of the first (or of a later) hemodynamic blood pressure measurement.

One embodiment of the present invention is a device 10 for measuring blood pressure hemodynamically in blood vessels at one or more body locations of a mammalian subject, the mammalian subject having a tissue. The device 10 comprises a light source 16 for shining light at the tissue under consideration so that the light either traverses the tissue of the body part of the subject or is reflected off the tissue (or in certain embodiments a combination of both). The light source is configured to shine light whose wavelength has any of the following ranges: visual range of 0.3 micron to 0.7 micron, near IR range of 0.7 micron to 5 micron, mid IR range of 5 micron to 40 micron and far IR range of 40 micron to 350 micron.

The device 10 also comprises at least three sensors 20 including an array of at least three optical sensors 20 for receiving the light that traverses and/or is reflected from the tissue of the mammalian subject and for obtaining a signal over time. The at least three optical sensors 20 are configured to receive a sequence of per pixel temporal information, for example color images, of the tissue, for example for each of three visible colors (for example red, green blue or yellow, magenta and cyan). In one example, the three visible colors have overlapping wavelengths. Each of the at least three optical sensors 20 of the array may be a photodetector and may have an absorption distribution function which decays outside of a finite range.

The signal obtained by the array of at least three optical sensors 20 comprises temporal per pixel information for at least two wavelengths of light. Although in some cases, the sensor 20 wavelength (of the array of optical sensors 20) may be the same as the wavelength of the light source 16, it should be clear that the sensor wavelength is not necessarily the same as the wavelength of the light source. For example, in one particular embodiment, the light from light source 16 is transmitted in the near IR range and the optical sensor senses the light in the visual range after the light is reflected from or traverses the tissue of the subject. The signal obtained by the array of at least three optical sensors 20 corresponds to a flow of blood within a blood vessel of the subject over time.

Device 10 also comprises hardware and software (collectively designated as "30") for supporting the array of at least three optical sensors 20 and any additional analog or optical sensors 20, and for converting the signal to a digital form (for example by means of an analog to digital convertor) in the event at least one of the additional sensors 20 is analog.

The hardware and software 30 of device 10 also comprises a processing unit 30 configured to receive the signal and generate a continuous dynamic blood pressure reading by using the temporal per pixel information for the at least two wavelengths of light to produce heart rate signals having a waveform. The heart rate signals are from the blood flow and include the subject's pulse (the pulse being a number). In addition, processing unit 30 is configured to apply a modified Windkessel model on the signal such that the blood pressure also depends on a spatial temporal pressure resistance function over time, wherein the pressure resistance function over time depends on a body location of the blood flow over time, and wherein the pressure resistance function represents at least one of (i) elastance or (ii) stiffness, of the blood vessel at a given body location and at a given time. The modified Windkessel model is described in detail in the discussions of equations (11) through (23), especially equations (15) through (23). For example equation (15) provides an extension of the Windkessel model, wherein solutions are provide in equations (19), (21) and (22).

As shown in FIG. 1B, the processing unit 30 in some embodiments has a medical subsystem that may use digital signal processing (DSP) to perform certain functions that may include calibrating illumination, configuring the sensors including the optical sensors and any other sensor in device 10, acquire the pixel information, process the images and extract clinical parameters like blood pressure. A further section of the processing unit 30 may also have a control subsystem in which a microcontroller provides a user interface, performs process management, internal storage and power management. A display is shown in a facade of the device 10 in FIG. 1A.

In some embodiments, the processing unit 30 is configured to produce the heart rate signals from the blood flow (i.e. heart rate signals having a waveform, which signals includes the subject's pulse) by averaging the per pixel information of the array per given time. In some embodiments, the processing unit 30 is configured to use the temporal per pixel information for the at least two wavelengths of light to produce at least one of (i) temporal histograms of light intensity for each wavelength of the at least two wavelengths, (ii) averaging the per pixel information of the array per given time and (iii) performing one or more algebraic operations by using the pixels information.

In some embodiments, the processing unit 30 is configured to use the temporal per pixel information for the at least two wavelengths of light to produce temporal histograms of light intensity for each wavelength of the at least two wavelengths.

In some embodiments, the processing unit 30 is configured to execute algebraic operations on the temporal per pixel information, for example to produce average(s) or ratios of the pixel information.

In some embodiments, while the signal over time is obtained, the array of the at least three optical sensors and/or one or more additional sensors are configured to also obtain and the processing unit is configured to also receive and process for increased accuracy of a blood pressure reading, at least one of the following: (a) local tissue perfusion using an optical sensor, (b) local tissue temperature using an optical sensor or thermometer, (c) volume and density of the blood tissue in the body location $X_0$ at which at least one optical sensor or ultrasound sensor 20U is used. In certain embodiments, while the signal over time is obtained, the array of the at least three optical sensors and/or one or more additional sensors are configured to also obtain and the processing unit is configured to also receive and process for increased accuracy of a blood pressure reading, at least two of the following: (a) local tissue perfusion using an optical sensor, (b) local tissue temperature using an optical sensor or thermometer, (c) volume and density of the blood tissue in the body location $X_0$ at which at least one optical sensor or ultrasound sensor 20U is used. In certain embodiments, while the signal over time is obtained, the array of the at least three optical sensors and/or one or more additional sensors are configured to also obtain and the processing unit is configured to also receive and process for increased accuracy of a blood pressure reading all of the following: (a) local tissue perfusion using an optical sensor, (b) local tissue temperature using an optical sensor or thermometer 20T, and (c) volume and density of the blood tissue in the body location $X_0$ at which at least one optical sensor or ultrasound sensor 20U is used.

Accordingly, device 10 may include, in addition to the three or more optical sensors, certain analog sensors 20 that are useful for improving the accuracy of the blood pressure reading, including by improving the accuracy of an initial blood pressure reading. However, the additional information for improving the accuracy of the blood pressure reading may instead be provided by the array of three optical sensors 20 and/or by additional optical sensors 20.

In certain embodiments, the processing unit 30 is configured to determine the hemodynamic blood pressure measurement (in some non-limiting cases this is an initial or a second or third hemodynamic blood pressure reading) using a resistance equation (21) of the form $$G(t) = \pm \frac{\alpha}{R_0}(t-t_d)^n,$$

where $t_d>0$, $\alpha$ and $R_0$ are constants and $n=0, 1, 2, 3, 4 \ldots,$.

In some embodiments, the device 10 further comprises an ultrasound component (which is an analog sensor 20 comprising one of the one or more additional sensors 20) configured to emit and receive ultrasound waves at the tissue of the blood vessel at the local location $X_0$ and to generate one or more signals corresponding to (a) the volume and/or density of the tissue at the particular body location and (b) a volume velocity of the blood flow in the tissue, wherein the processing unit is configured to receive output from the ultrasound component 20U to increase an accuracy of a blood pressure reading especially, but not limited to, by estimating an initial blood pressure reading.

In certain embodiments, for example as shown in FIG. 2, the at least three sensors 20 include an array of at least three optical sensors 20, an ultrasound sensor 20U and a thermometer 20T. The thermometer 20T may include a thermometer for measuring local tissue temperature, which may be an optical or analog thermometer 20T.

Figure 7:
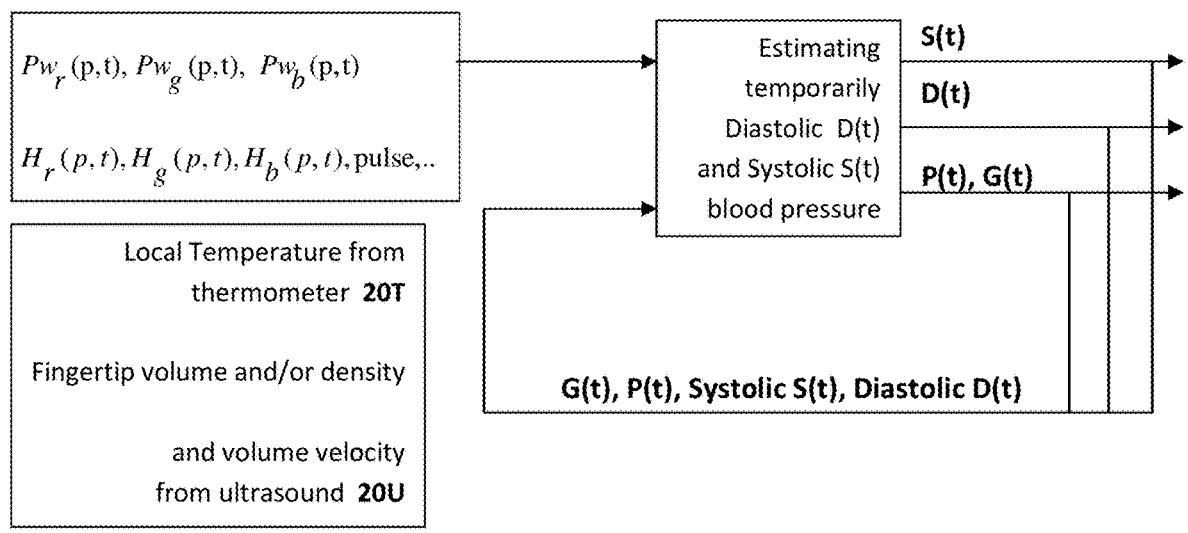
FIG. 7 is a schematic of a feedback mechanism used in the method, system and device, in accordance with one embodiment of the present invention.

Although in some embodiments, the device 10 is configured to obtain the blood pressure as the blood flows through the body of the mammalian subject, in certain other embodiments, the processing unit 30 of device 10 is configured to provide the blood pressure at a particular body location, $X_0$, of the mammalian subject. In this case, the pressure resistance function is a spatial temporal function that measures the resistance and/or elastance of the blood vessel at the particular body location, $X_0$, over time.

g) Feedback:

The Feedback mechanism allows better control of the pressure flow during beat2beat flow. In certain embodiments, the feedback machine has the following structure, as shown in FIG. 7.

Annex A

---

Let
1. $F(t) = P(t) \cdot G(t) + c \cdot P'(t)$ where c is constant
Define

2. $\emptyset(t) = c \cdot e^{c^{-1}\int G(t)dt} = c \cdot e^{\frac{1}{c}\int G(t)dt}$ Then, 3. $\frac{d}{dt}(\emptyset(t) \cdot P(t)) = \emptyset'(t) \cdot P(t) + \emptyset(t) \cdot P'(t) =$ 4. $e^{c^{-1}\int G(t)dt} \cdot (P(t) \cdot G(t) + c \cdot P'(t)) = e^{c^{-1}\int G(t)dt} \cdot F(t)$ Multiplying Eq. (1) by $\emptyset(t)$ and taking (3) and (4) under consideration we get 5. $\emptyset(t) \cdot P(t) = \int e^{c^{-1}\int G(u)du} \cdot F(t) \cdot dt + L$, where L is constant From (5) we conclude, 6. $P(t) = c^{-1} \cdot e^{-c^{-1}\int G(t)dt} \cdot \int e^{c^{-1}\int G(u)du} \cdot F(t) \cdot dt + c_1 \cdot e^{-c^{-1}\int G(t)dt},$ where $c_1 = \frac{L}{C}$ In case $G(t) = \frac{\alpha}{R}$ where R is the constant resistance then Eq. (6) gets the following form 7. $P(t) = c^{-1} \cdot e^{-\frac{\alpha(t-t_d)}{c \cdot R}} \cdot \int e^{\frac{\alpha(t-t_d)}{c \cdot R}} \cdot F(t) \cdot dt + c_1 \cdot e^{-\frac{\alpha(t-t_d)}{c \cdot R}},$

---

Results and Discussion of Clinical Trials

The TensorTip device 10 and its method utilizing a mathematical model for computing hemodynamic blood pressure were subjected to various clinical trials. Post marketing has been executed. The first clinical trial was executed in Carmel and Lin Daycare Medical Centers (Haifa, Israel) on ambulatory patients from the liver and diabetes daycare clinics and on healthy participants as well. Results were compared with manual and automatic arm cuff blood pressure measurements. An additional trial was carried out in the Morristown Memorial Medical Center (MMMC) located in New Jersey, USA. The trial was conducted in the ICU (Intensive Care Unit) on patients recovering after heart surgery, compared to an in line blood pressure sensor.

A total of 118 members participated in these two studies, giving a total of 603 measurements. In the MMMC study 330 measurements were taken from 64 patients, while in the Carmel & Lin Medical centers study 273 measurements were taken from 54 participants.

Testing environment conditions were asked from the participants in the Carmel & Lin Medical clinical trial: being in-door, at normal room temperature and in a seating position. Three arm-cuff references readings were taken from each participant during this study. Reference devices included two automatic oscillometric blood pressure monitors and one manual oscillometric blood pressure monitor. The most agreeable result was considered between the references and the TensorTip MTX.

In the MMIVIC study patients were monitored in Intensive Care Unit (ICU) with their equipment and by experienced critical care nurses. Readings were taken by the TensorTip MTX and were compared to a stable in line hemodynamic monitor. The TensorTip MTX readings were compared to the in-line arterial tube readings. It should be mentioned that a small number of tests (~7.5%) were not able to be assessed by the TensorTip device in the MMMC trial. This was presumed to be related to a local hypothermia state following a cardiac surgery, resulted in low blood pressure due to low blood perfusion in the fingertip.

Figure 8:
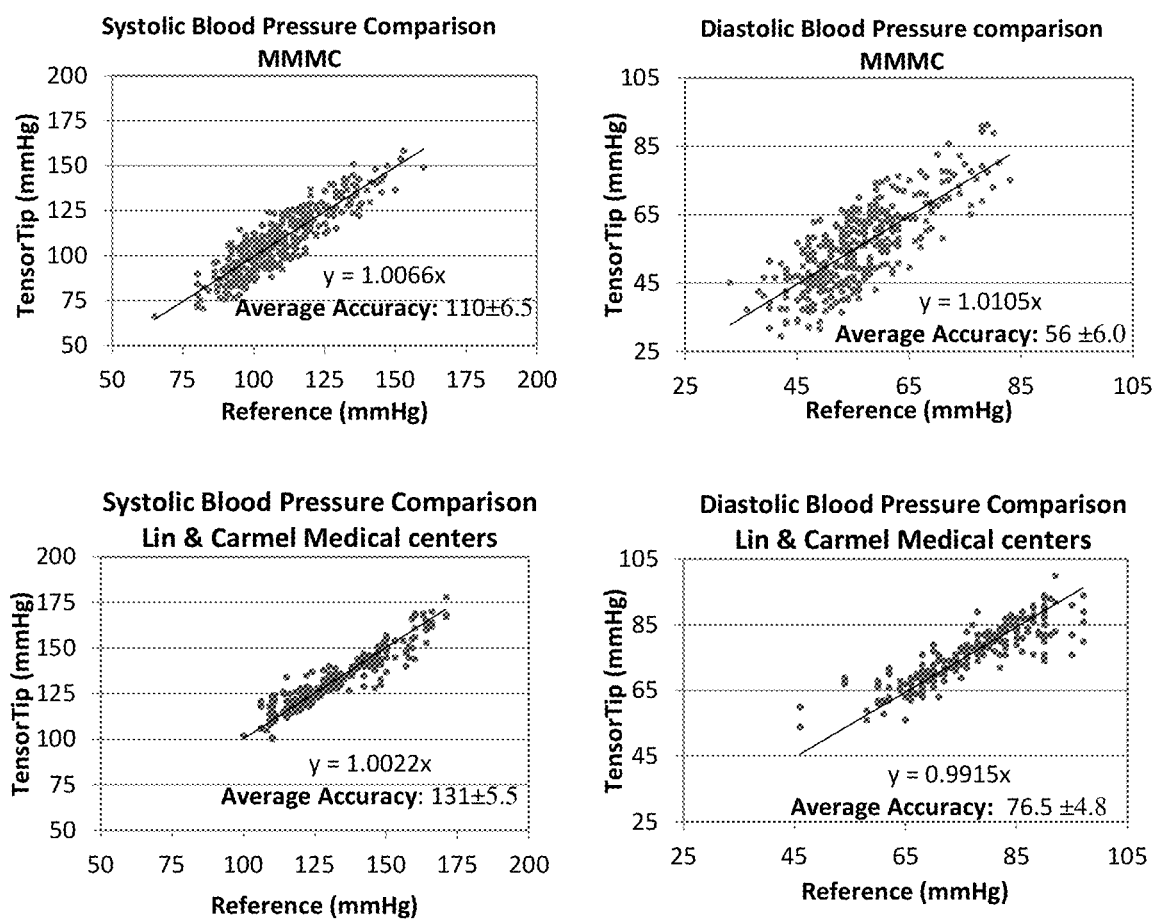
FIG. 8 shows a comparison in graph form of systolic and diastolic blood pressure among patients in two separate studies, one conducted in MM Medical Center and the other conducted in the Carmel & Lin Medical centers, in accordance with one embodiment of the present invention.

FIG. 8 displays the systolic and diastolic blood pressure measurements comparison between the TensorTip and the reference measurements in two different clinical studies. For the MMMC trial, the average of the referenced hemodynamic measurements was 107.76 and 56.22 mmHg for the systolic and diastolic blood pressure respectively. For the TensorTip, the average was 100.71 and 55.18 mmHg for the systolic and diastolic blood pressure, respectively. Consequently, the standard deviation (SD) was 7.9 mmHg for the systolic blood pressure, and 7.5 mmHg for the diastolic blood pressure. For the Lin & Carmel Medical centers trial, the average of the reference was 131.23 and 76.51 mmHg for the systolic and diastolic blood pressure, correspondingly. Whereas for the TensorTip, the average was 131.80 and 76.16 mmHg systolic and diastolic blood pressure, respectively. Thus the SD was 5.5 mmHg for the systolic blood pressure, and 4.7 mmHg for the diastolic blood pressure. It should be mentioned that the most satisfying reference was chosen. Therefore, for blood pressure measurements, the mean absolute error is not higher than |8 mmHg| for systolic and diastolic. This means that the TensorTip blood pressure measurements fulfill the ISO 81060-2 recognized standard requirements.

Figure 9:
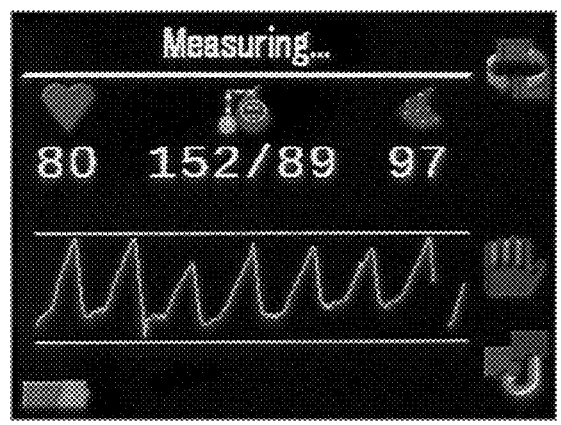
FIG. 9 shows a display screen of the device showing a peripheral pulse waveform and above it several hemodynamic parameters, including the measured pulse, the blood pressure and SpO2, in accordance with one embodiment of the present invention.

As was described above, the TensorTip device can measure several hemodynamic parameters; among them are blood pressure and Mean Arterial Pressure (MAP). The obtained values are displayed on the device's screen as illustrated in FIG. 9. The number shown at the left represents the measured pulse; the numbers at the middle signify the blood pressure; and the number at the right stands for SpO2. Additional bio parameters are shown in the next screens of the device such as Hb, Hct, C.O, SV, etc. FIG. 9 is a Peripheral Pulse Waveform.

Figure 10:
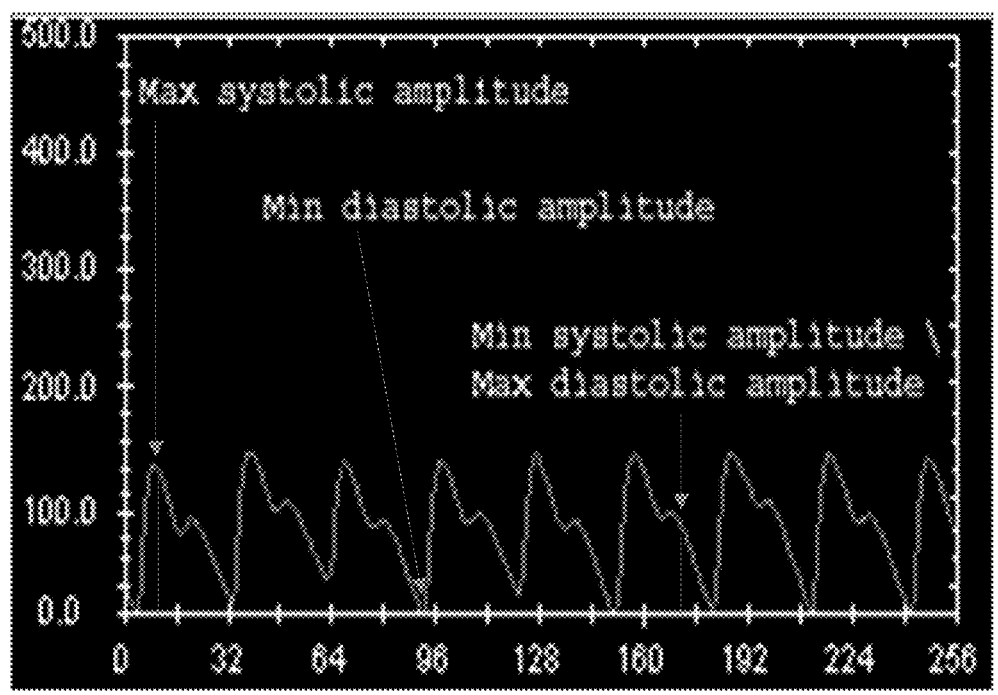
FIG. 10 shows a display screen of the device showing computed P(t) pressure waveform normalized to zero, in accordance with one embodiment of the present invention.

FIG. 10 below displays the computed P(t) pressure waveform normalized to zero. The highest amplitude represents the max systolic peak, which decreases until reaching a point on the graph slope denoted by the min systolic amplitude that also stands for the max diastolic amplitude. From that point the amplitude decreases until reaching min diastolic amplitude which is normalized to zero. Diastolic base pressure is detected from the P(t) curve.

Figure 11:
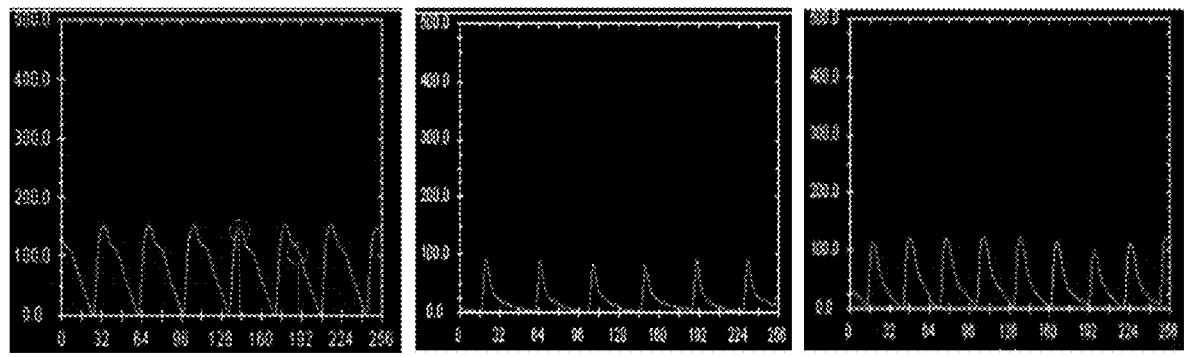
FIG. 11 shows a display screen of three different measurements of the systolic and diastolic amplitudes from a blood pressure P(t) waveform, in accordance with one embodiment of the present invention.

FIG. 11 displays different measurements of the systolic and diastolic amplitudes. The left picture shows a relatively high systolic and diastolic blood pressure P(t) waveform, while the middle picture indicates on a low diastolic pressure and cardiac output. The right picture demonstrates a diastolic pressure which is quite normal with relatively improved cardiac output. FIG. 11: Left picture indicates on relatively high systolic and diastolic blood pressure waveform. The middle picture of FIG. 11 indicates that the diastolic pressure and cardiac output are relatively low, while the picture on the right indicates that the diastolic pressure is relatively normal with relatively improved cardiac output compared with the middle and the left pictures.

Figure 12:
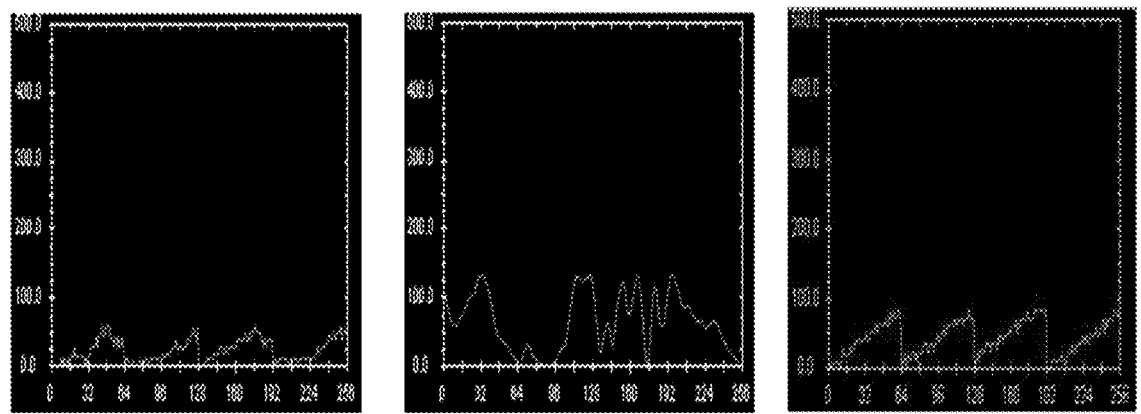
FIG. 12 shows a display screen of three different types of noisy pressure waveform P(t) resulting from noisy input signals, in accordance with one embodiment of the present invention.

FIG. 12 shows three different types of noisy pressure waveform P(t) resulting from noisy input signals. Those noisy signals may result from hypothermia (i.e. cold fingers) or low blood perfusion.

Geyser

Figures 13A, 13B, 13C:
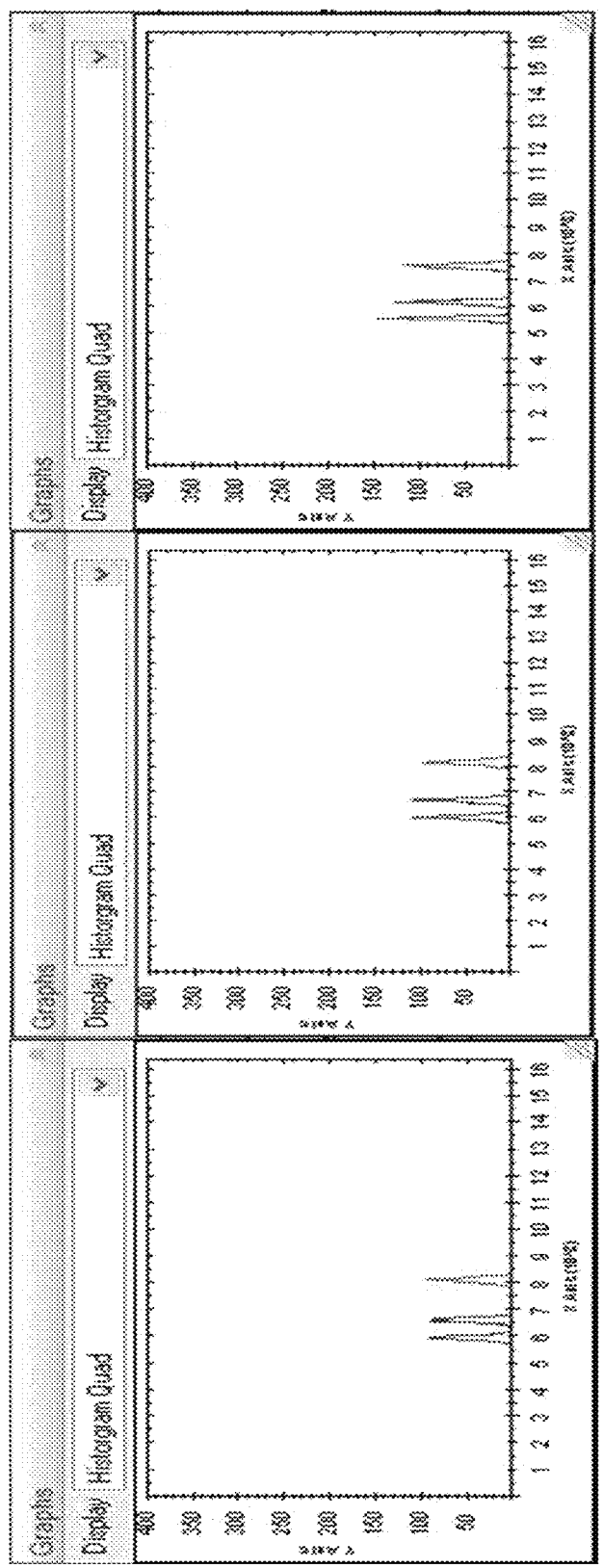
FIG. 13A shows a normal temporal color histogram resulting from diastole pressure flow, in accordance with one embodiment of the present invention.
FIG. 13B shows a temporal color histogram with volume increasing due to systolic pressure rising, in accordance with one embodiment of the present invention.
FIG. 13C shows a temporal color histogram with a cyclic, relatively high burst in the leftmost histogram plot (associated with blue) of the systolic pressure, in accordance with one embodiment of the present invention.
Figure 14:
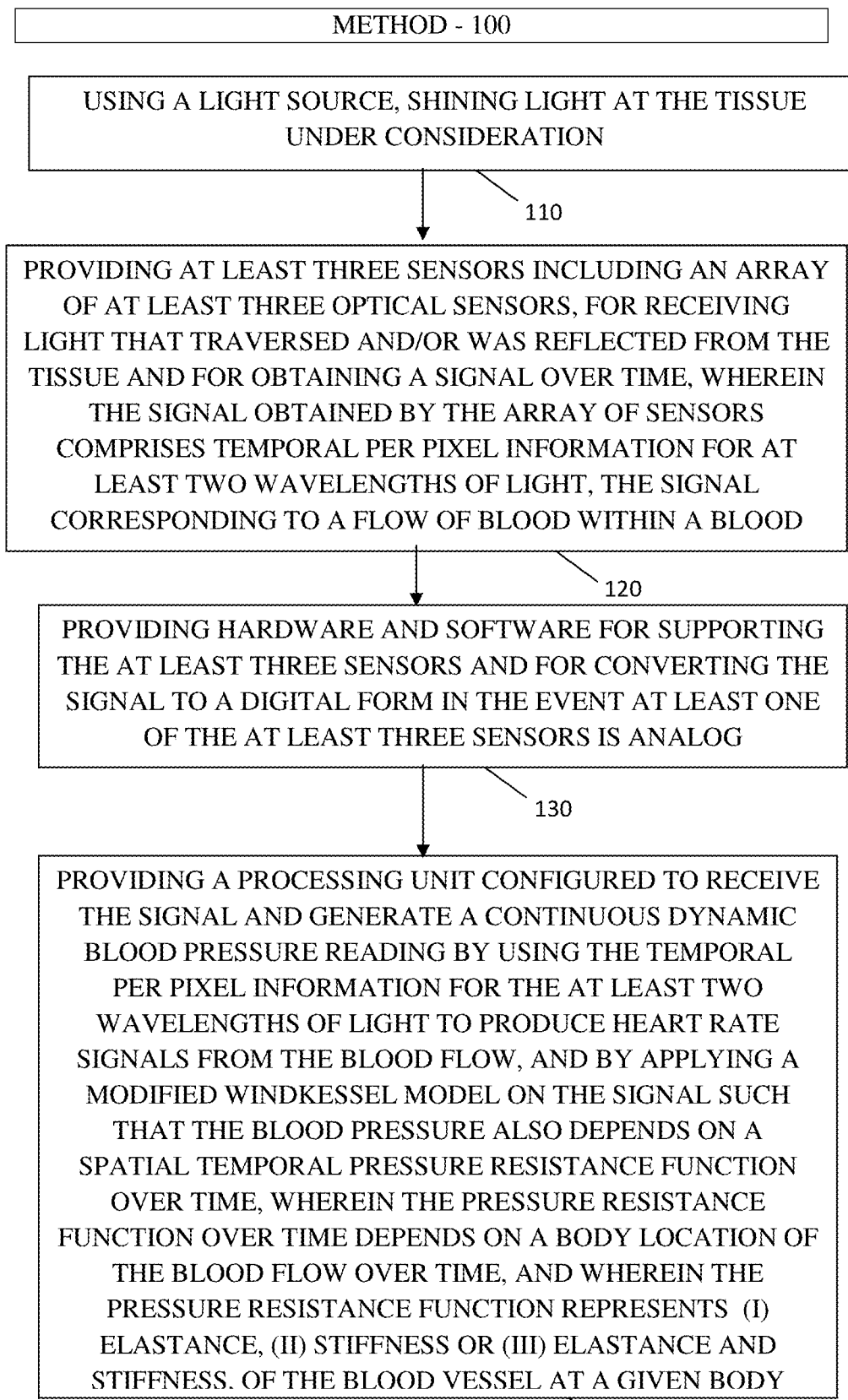
FIG. 14 is a flow chart of a method, in accordance with one embodiment of the present invention.

During Applicant's investigation Applicant discovered a phenomenon of the temporal color histograms that it named "Geyser". It called a relatively high cyclic temporal peak of at least one of the temporal color histograms a "geyser". In FIG. 13 one can identify a burst in the blue color histogram. The burst may be shifted to the other colors. Applicant considers this burst a "geyser" if the burst is cyclic (repeats itself, no matter in which color) and is relatively high compared with a normal burst caused by the heart. What Applicant has found is that not every subject has this "geyser" phenomenon. For some people, Applicant identified the geyser and for others just a normal burst. This identification is useful and it may be that having a geyser or the lack of indicate an abnormal potential activity. Further studies still need to be done to determine this. FIG. 13A: (Left) shows normal histogram volume resulting from diastole pressure flow; FIG. 13B: (Middle) shows Volume is increasing due to systolic rising; FIG. 13C: (Right) shows an outburst of the systolic pressure, named "geyser", presented in the blue peak. Since FIGS. 13A-13C are in black and white, for clarity it is noted that in each of FIGS. 13A, 13B and 13C, going from left to right along the X axis, the respective histogram plots are first the blue, then the green and then the red.

One embodiment of the present invention is a method 100 for measuring blood pressure hemodynamically in blood vessels at one or more body locations of a mammalian subject, the mammalian subject having a tissue, comprising a step 110 of using a light source, shining light at the tissue under consideration. A further step 120 is providing at least three sensors including an array of at least three optical sensors, for receiving light that traversed and/or was reflected from the tissue and for obtaining a signal over time, wherein the signal obtained by the array of sensors comprises temporal per pixel information for at least two wavelengths of light, the signal corresponding to a flow of blood within a blood vessel of the subject over time. A further step 130 is providing hardware and software for supporting the at least three sensors and for converting the signal to a digital form in the event at least one of the at least three sensors is analog. A still further step 140 is providing a processing unit configured to receive the signal and generate a continuous dynamic blood pressure reading by using the temporal per pixel information for the at least two wavelengths of light to produce heart rate signals from the blood flow, and by applying a modified Windkessel model on the signal such that the blood pressure also depends on a spatial temporal pressure resistance function over time, wherein the pressure resistance function over time depends on a body location of the blood flow over time, and wherein the pressure resistance function represents (i) elastance, (ii) stiffness or (iii) elastance and stiffness, of the blood vessel at a given body location and at a given time.

In some embodiments of the method there is a step of having the light source shine light whose wavelength has any of the following ranges: visual range of 0.3 micron to 0.7 micron, near IR range of 0.7 micron to 5 micron, mid IR range of 5 micron to 40 micron and far IR range of 40 micron to 350 micron. In some embodiments of the method, the processing unit is configured to produce the heart rate signals by averaging the per pixel information of the array per given time. In some embodiments of the method, the processing unit is configured to determine the hemodynamic blood pressure measurement using a resistance equation (21) of the form $$G(t) = \pm \frac{\alpha}{R_0}(t-t_d)^n,$$

where $t_d > 0$, $\alpha$ and $R_0$ are constants and n=0, 1, 2, 3, 4 . . . , .

In some embodiments of the method, there is a step comprising, while the signal over time is obtained, having the array of at least three optical sensors and/or one or more additional sensors also obtain and the processing unit also receive and process for increased accuracy of a blood pressure reading, at least one (or at least two or all three) of the following: (a) local tissue perfusion using an optical sensor, (b) local tissue temperature using an optical sensor or thermometer, (c) volume and density of the blood tissue in the body location $X_0$ at which at least one optical sensor or ultrasound sensor is used.

In some embodiments of the method, there is a step of having the processing unit provides the blood pressure at a particular body location, $X_0$, of the mammalian subject, wherein the pressure resistance function is a spatial temporal function that measures the resistance or elastance of the blood vessel at the particular body location, $X_0$, over time.

In some embodiments of the method, there is a step of emitting and receiving, using an ultrasound component, ultrasound waves at the tissue of the blood vessel at the local location $X_0$ and to generate one or more signals corresponding to (a) the volume and/or density of the tissue at the particular body location and (b) a volume velocity of the blood flow in the tissue, wherein the processing unit is configured to receive output from the ultrasound component to increase an accuracy of a blood pressure reading by estimating an initial blood pressure reading.

In some embodiments of the method there is a step of having the processing unit use the temporal per pixel information for the at least two wavelengths of light to produce at least one of (i) temporal histograms of light intensity for each wavelength of the at least two wavelengths and (ii) averaging the per pixel information of the array per given time. In some other embodiments of the method there is a step of having the processing unit use the temporal per pixel information for the at least two wavelengths of light to produce temporal histograms of light intensity for each wavelength of the at least two wavelengths. In some other embodiments of the method there is a step of having the processing unit apply algebraic operations to the temporal per pixel information for the at least two wavelengths of light.

While the invention has been described with respect to a limited number of embodiments, it will be appreciated that many variations, modifications and other applications of the invention may be made. Therefore, the claimed invention as recited in the claims that follow is not limited to the embodiments described herein.

What is claimed is:

1. A device for measuring blood pressure hemodynamically in blood vessels at one or more body locations of a mammalian subject, the mammalian subject having a tissue, comprising:
    a light source for shining light at the tissue under consideration;
    at least three sensors including an array of at least three optical sensors, for receiving light that traversed and/or was reflected from the tissue and for obtaining a signal over time, wherein the signal obtained by the array of sensors comprises temporal per pixel information for at least two wavelengths of light, the signal corresponding to a flow of blood within a blood vessel of the subject over time;
    hardware and software for supporting the at least three sensors and for converting the signal to a digital form in the event at least one of the at least three sensors is analog,
    the hardware and software also comprising a processing unit configured to receive the signal and generate a continuous dynamic blood pressure reading by using the temporal per pixel information for the at least two wavelengths of light to produce heart rate signals from the blood flow, and by applying a modified Windkessel model on the signal such that the blood pressure also depends on a spatial temporal pressure resistance function over time, wherein the pressure resistance function over time depends on a body location of the blood flow over time, and wherein the pressure resistance function represents (i) elastance, (ii) stiffness or (iii) elastance and stiffness, of the blood vessel at a given body location and at a given time; and
    a display configured to display the continuous dynamic blood pressure reading.

2. The device of claim 1, wherein the light source is configured to shine light whose wavelength has any of the following ranges: visual range of 0.3 micron to 0.7 micron, near IR range of 0.7 micron to 5 micron, mid IR range of 5 micron to 40 micron and far IR range of 40 micron to 350 micron.

3. The device of claim 1, wherein the processing unit is configured to produce the heart rate signals by averaging the per pixel information of the array per given time.

4. The device of claim 1, wherein the processing unit is configured to determine the hemodynamic blood pressure measurement using a resistance equation (21) of the form $$G(t) = \pm \frac{\alpha}{R_0}(t-t_d)^n,$$

where $t_d > 0$, $\alpha$ and $R_0$ are constants and n=0, 1, 2, 3, 4 . . . , .

5. The device of claim 1, wherein, while the signal over time is obtained, the array of at least three optical sensors and/or one or more additional sensors are configured to also obtain and the processing unit is configured to also receive and process for increased accuracy of a blood pressure reading, at least one of the following: (a) local tissue perfusion using an optical sensor, (b) local tissue temperature using an optical sensor or thermometer, (c) volume and density of the blood tissue in the body location $X_0$ at which at least one optical sensor or ultrasound sensor is used.

6. The device of claim 1, wherein, while the signal over time is obtained, the array of at least three optical sensors and/or one or more additional sensors are configured to also obtain and the processing unit is configured to also receive and process for increased accuracy of a blood pressure reading, at least two of the following: (a) local tissue perfusion using an optical sensor, (b) local tissue temperature using an optical sensor or thermometer, (c) volume and density of the blood tissue in the body location $X_0$ at which at least one optical sensor or ultrasound sensor is used.

7. The device of claim 1, wherein, while the signal over time is obtained, the array of at least three optical sensors and/or one or more additional sensors are configured to also obtain and the processing unit is configured to also receive and process for increased accuracy of a blood pressure reading all of the following: (a) local tissue perfusion using an optical sensor, (b) local tissue temperature using an optical sensor or thermometer, and (c) volume and density of the blood tissue in the body location $X_0$ at which at least one optical sensor or ultrasound sensor is used.

8. The device of claim 1, wherein the processing unit is configured to provide the blood pressure at a particular body location, $X_0$, of the mammalian subject, wherein the pressure resistance function is a spatial temporal function that measures the resistance or elastance of the blood vessel at the particular body location, $X_0$, over time.

9. The device of claim 1, further comprising an ultrasound component configured to emit and receive ultrasound waves at the tissue of the blood vessel at the local location $X_0$ and to generate one or more signals corresponding to (a) the volume and/or density of the tissue at the particular body location and (b) a volume velocity of the blood flow in the tissue,
wherein the processing unit is configured to receive output from the ultrasound component to increase an accuracy of a blood pressure reading by estimating an initial blood pressure reading.

10. The device of claim 1, wherein the processing unit is configured to use the temporal per pixel information for the at least two wavelengths of light to produce at least one of (i) temporal histograms of light intensity for each wavelength of the at least two wavelengths and (ii) averaging the per pixel information of the array per given time.

11. The device of claim 1, wherein the processing unit is configured to use the temporal per pixel information for the at least two wavelengths of light to produce temporal histograms of light intensity for each wavelength of the at least two wavelengths.

12. The device of claim 1, wherein the processing unit is configured to apply algebraic operations to the temporal per pixel information for the at least two wavelengths of light.

13. The method of claim 1, further comprising having the processing unit determine the hemodynamic blood pressure measurement using a resistance equation (21) of the form $$G(t) = \pm \frac{\alpha}{R_0}(t - t_d)^n,$$

where $t_d > 0$, $\alpha$ and $R_0$ are constants and $n = 0, 1, 2, 3, 4 \ldots,$.

14. A method for measuring blood pressure hemodynamically in blood vessels at one or more body locations of a mammalian subject, the mammalian subject having a tissue, comprising:
using a light source, shining light at the tissue under consideration;
providing at least three sensors including an array of at least three optical sensors, for receiving light that traversed and/or was reflected from the tissue and for obtaining a signal over time, wherein the signal obtained by the array of sensors comprises temporal per pixel information for at least two wavelengths of light, the signal corresponding to a flow of blood within a blood vessel of the subject over time;
providing hardware and software for supporting the at least three sensors and for converting the signal to a digital form in the event at least one of the at least three sensors is analog;
providing a processing unit configured to receive the signal and generate a continuous dynamic blood pressure reading by using the temporal per pixel information for the at least two wavelengths of light to produce heart rate signals from the blood flow, and by applying a modified Windkessel model on the signal such that the blood pressure also depends on a spatial temporal pressure resistance function over time, wherein the pressure resistance function over time depends on a body location of the blood flow over time, and wherein the pressure resistance function represents (i) elastance, (ii) stiffness or (iii) elastance and stiffness, of the blood vessel at a given body location and at a given time; and
displaying the continuous dynamic blood pressure reading on a display.

15. The method of claim 14, further comprising,
while the signal over time is obtained, having the array of at least three optical sensors and/or one or more additional sensors obtain and the processing unit also receive and process for increased accuracy of a blood pressure reading, at least one of the following: (a) local tissue perfusion using an optical sensor, (b) local tissue temperature using an optical sensor or thermometer, (c) volume and density of the blood tissue in the body location $X_0$ at which at least one optical sensor or ultrasound sensor is used.

* * * * *